United States Patent [19]

Sinko

[11] 4,306,566
[45] Dec. 22, 1981

[54] CHOLANGIOGRAM CATHETER

[75] Inventor: George E. Sinko, San Antonio, Tex.

[73] Assignee: Gesco International, Inc., San Antonio, Tex.

[21] Appl. No.: 154,214

[22] Filed: May 29, 1980

Related U.S. Application Data

[63] Continuation of Ser. No. 913,443, Jun. 7, 1978, abandoned.

[51] Int. Cl.³ ............................................. A61M 25/00
[52] U.S. Cl. ...................................... 128/658; 128/348
[58] Field of Search ........ 128/349 B, 349 R, 349 BV, 128/348, 214 R

[56] References Cited

U.S. PATENT DOCUMENTS

| | | | |
|---|---|---|---|
| 504,424 | 9/1893 | Pezzer | 128/349 R |
| 1,045,326 | 11/1912 | Ruflin | 128/349 R |
| 1,888,349 | 11/1932 | Jacoby | 128/349 R |
| 2,976,865 | 3/1961 | Shipley | 128/349 R |
| 3,958,557 | 5/1976 | Sharp et al. | 128/348 |
| 4,116,227 | 9/1978 | Eisenberg et al. | 128/349 R |
| 4,122,858 | 10/1978 | Schiff | 128/348 |
| 4,173,228 | 11/1979 | Steenwyk | 128/349 R |

Primary Examiner—Richard C. Pinkham
Assistant Examiner—T. Brown

[57] ABSTRACT

A catheter for injecting a contrast medium in the biliary tract as part of the surgical procedure in gallstone removal and related procedures. The cholangiogram catheter utilizes a small section of plastic tubing to which is attached a stainless steel conical tip. To the opposite end of the plastic tubing is secured a syringe adapter for receiving the tip of an injection syringe frequently utilized by doctors and nurses. In assembling the device, a ligature gap is created adjacent the flare of the conical tip to facilitate an effective closing of a duct adjacent the conical tip and plastic tubing.

1 Claim, 6 Drawing Figures

CHOLANGIOGRAM CATHETER

This is a continuation of application Ser. No. 913,443, filed June 7, 1978, abandoned.

BACKGROUND OF THE INVENTION

In surgical procedures it is frequently necessary to insert tubes for injecting contrast mediums into arteries, ducts, and veins preliminary to or as a part of the surgical procedure. In inserting these tubes, hemostats, forceps or other clamp-like structures must be utilized to grip the instrument adjacent the tip for insertion in the vein or duct. Additional steps in the surgical procedure frequently necessitate the closure of the duct around the instrument adjacent the tip. Leakage can occur in this area. Inadvertent induction of air into the procedures hampers the test such as air in the biliary tree can appear on x-rays as a gallstone.

FIELD OF THE INVENTION

This invention pertains to the construction of a tube particularly designed for inserting in a cystic duct utilizing a ligature for closing the duct around the catheter sealing against leakage or induction of air. The device of this invention employs a stainless steel conical tip securely affixed to the plastic tubing. The elongated section of plastic tubing has a syringe adapter secured to the end of the tubing opposite the conical tip. A portion of the method of construction pertains to an improved device and procedure for securely affixing the conical tip to the tubing.

DESCRIPTION OF THE PRIOR ART

Catheters are extremely old in the medical field. Rubber and plastic catheters are utilized in numerous medical and surgical procedures and have been developed in various configurations, some of which have been patented. Plastic or rubber structures having integral tips create problems in their gripping by hemostats or forceps in the insertion in that the plastic is deformed and the tips could become detached. This fact prompted your inventor to develop a secure stainless steel tip for transparent tubing creating a structure lending itself to grasping by surgical instruments inserting into a duct and to a secure seal with a ligature encircling the duct adjacent the tip of the catheter.

SUMMARY OF THE INVENTION

A principal object of this invention was to construct a catheter particularly suitable for utilization in a cholangiographic procedure producing by x-ray cholangiography. The instrument of this invention is aptly described as a cholangiogram catheter. This application is designed to apply to the structure of an improved cholangiogram catheter. The description of the preferred embodiment will describe both the device and the machine or method for construction or assembly.

The device of this invention pertains to an improved cholangiogram catheter 10 utilizing a stainless steel tip 11 to which is secured a section of plastic tubing 15 which is assembled in a particular configuration creating a ligature gap 16 adjacent the conical tip. The space between the flange 17 of conical tip 12 and the plastic tubing 15 creates a ligature gap 16 particularly adaptable in the surgical or test procedures for which the cholangiogram catheter 10 of this invention was designed.

BRIEF DESCRIPTION OF THE DRAWINGS

For a detailed description of the construction of the device of this invention and the assembly thereof, reference is made to the attached several views wherein identical reference characters will be utilized and refer to identical or equivalent components throughout the several views and the following detailed description of the preferred embodiment.

DESCRIPTION OF THE PREFERRED EMBODIMENT

Figure 1:
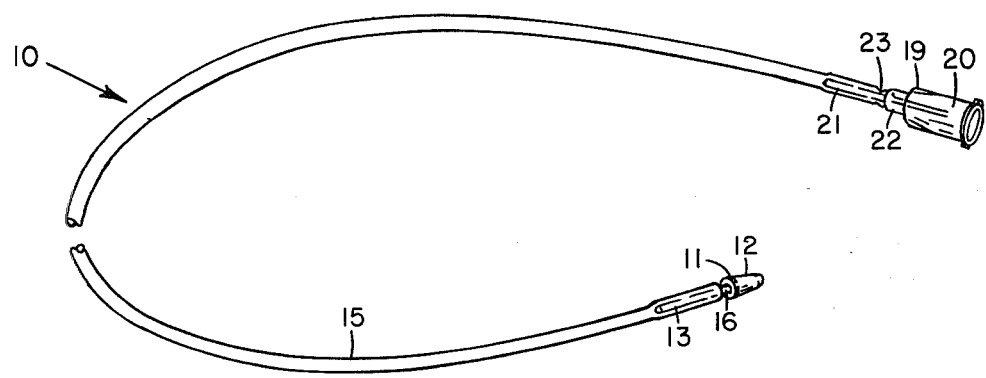
FIG. 1 is a plan, assembled view of the cholangiogram catheter illustrating the device including the stainless steel tip, plastic tubing and the syringe adapter.
Figure 2:
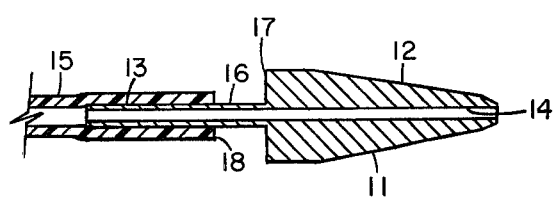
FIG. 2 is an enlarged, sectional view of the stainless steel tip with a fragmented section of tubing attached.
Figure 4:
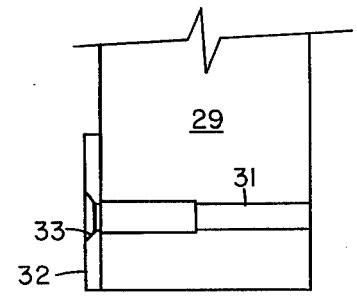
FIG. 4 is a partially fragmented view of the pneumatic vise illustrating the vise base and the configuration of the tubing channel and face plate centering guide.
Figure 5:
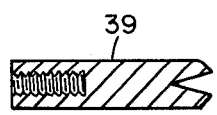
FIG. 5 is a sectional view of a tip die.
Figure 6:
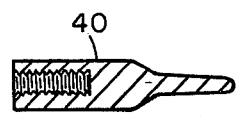
FIG. 6 is a sectional view of a cup die.

For a description of the preferred embodiment, reference is particularly made to FIGS. 1 and 2. Cholangiogram catheter 10 is constructed with a stainless steel tip 11. Conical tip 12 is ¼" long, whereas the overall length of the stainless steel tip 11 is ¾". The base of the conical tip 12 is 91/1000" in diameter and the shaft of the conical tip 12 is 35/1000". The shaft 13 is approximately ½" in length and the aperture 14 projecting through shaft 13 and conical tip 12 is 20/1000". The stainless steel tip is press fitted in assembly onto an 18" piece of plastic tubing 15. "Tenite", a plastic tubing produced by Eastman Kodak Co., was successfully used in the preferred embodiment. The plastic tubing 15 has an outside diameter of 60/1000" to 65/1000" and an inside diameter of 29/1000" to 30/1000". In the final assembly of this device, the ligature gap 16 is formed between the flange 17 of the conical tip 12 and the flange 18 of plastic tubing 15. This ligature gap 16 permits the tightening of a ligature around a duct or vein securing the duct or vein into the ligature gap 16 forming a highly satisfactory seal against leakage or induction of air into the duct or vein being subjected to the surgical procedure. The cobined action on the duct of the ligature gap 16, the flange 17 of conical tip 12 and the flange 18 of the plastic tubing 15 contributes to this improved seal against leakage. Secured to the opposite end of plastic tubing 15 is a syringe adapter 19. This structure is sometimes referred to as a blunt needle. This syringe adapter 19 is press fitted into plastic tubing 15 and crimped for maximum securing. The assembled device as illustrated in FIG. 1 includes the plastic cup 20 receiving a surgical syringe. Secured to the plastic cup 20 is syringe shaft 13 which is formed integral with plastic cup 20 by shaft base 22. In the assembly procedure which will be discussed in detail later in the application, the machine assembling the device creates a tubing crimp 23 adjacent shaft base 22. The foregoing generally describes the material and construction of the cholangiogram catheter of this invention.

METHOD OF CONSTRUCTION AND PROCEDURES FOR ASSEMBLY

Figure 3:
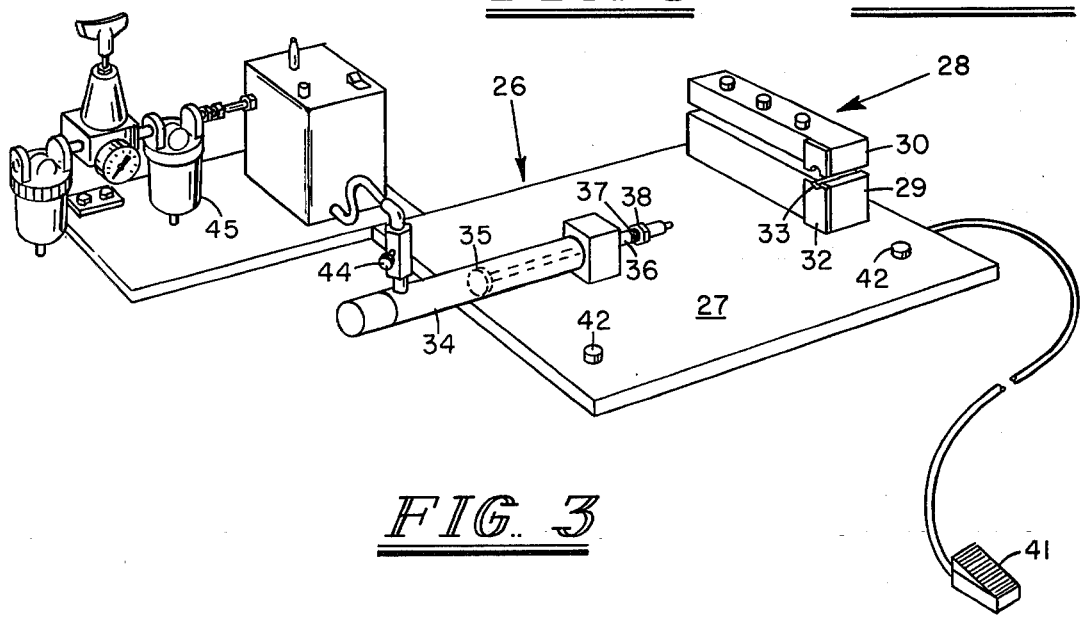
FIG. 3 is a perspective view of the machine for practicing a method of assembly of the device of this invention.

The device for assembling the components of this invention is generally described in FIG. 3. The device may be referred to as a pneumatic press 26 which is supported by mounting base 27 which is constructed of such configuration as to be supported on a table-like structure. A portion of the assembly as illustrated comprises a pneumatic vise 28 which is generally utilized to retain the plastic tubing 15 in the assembly process. Pneumatic vise 28 is constructed with a vise base 29 and a vise jaw 30. The vise base 29 and the vise jaw 30 are constructed with a tubing channel 31 having a particular configuration for securely grasping and retaining the plastic tubing 15 in the assembly process. The tubing channel 31 at the end through which the extended length of plastic tubing 15 projects has an inside diameter of 50/1000". The diameter of tubing channel 31 adjacent the face plate 32 is 65/1000" in diameter to permit some expansion of the plastic tubing 15 in the forced fit assembly process. Face plate 32 is constructed with a tapered centering cone 33 having a flared configuration for receiving shaft 13 of conical tip 12 in one portion of the assembly process or syringe shaft 21 in another portion of the assembly process. In operation of the device, pressure regulating valves are desirable and the pressure under which pneumatic vise 28 operates is normally 110 psi. A short distance from the pneumatic vise 28 is positioned in an operable relationship pneumatic cylinder 34 which contains a pneumatic piston 35 to which is secured a pneumatic shaft 36 projecting in an operable relationship toward pneumatic vise 28. The end of pneumatic shaft 36 is constructed with a shaft threaded portion 27 to which is loosely secured a stop nut 38 adapting the pneumatic shaft 36 to receive a tip die 39 which will loosely engage a conical tip 12 with a shaft 13 projecting in the direction of vise 28. In the process for attaching a stainless steel tip 11 to the plastic tubing 15, conical tip 12 projects into the tip die 39 and a section of plastic tubing 15 is gripped by pneumatic vise 28, activating pneumatic cylinder 34 by applying approximately 12 psi to the pneumatic piston 35 projecting the shaft 13 through centering cone 33 into tubing channel 31 securely implanting shaft 13 into plastic tubing 15. This assembly process results in the leaving or forming of the ligature gap 16 adjacent the flange 17 of cone 12 and the flange 18 of tubing 15. A similar procedure is utilized in attaching the syringe adapter 19 to the opposite end of plastic tubing 15. A different adapter must be secured to the pneumatic shaft 36. An adapter designed to fit into the syringe adapter 19 is secured to the shaft threaded portion 37 and affixed by rotation of stop nut 38. Cup die 40 projects into syringe adapter 19 and the section of plastic tubing 15 is retained in pneumatic vise 28. Vise actuating pedal 41 is pressed admitting the 110 psi to the vise securely grasping plastic tubing 15 after which piston activating button 42 is depressed admitting 12 psi to the pneumatic piston 35. This procedure in its first step firmly implants the syringe shaft 21 interior of plastic tubing 15. After this initial step, the plastic tubing 15 may be projected to a position approximately adjacent the surface of face plate 32 and the vise activating pedal 41 again pressed. This procedure results in a gripping of the plastic tubing 15 adjacent shaft base 22 forming the tubing crimp 23 around syringe shaft 21. The characteristic of "Tenite" plastic tubing 15 is that it retains this pressure crimp configuration forming a very secure seal on the syringe adapter 19 to plastic tubing 15.

OPERATION OF THE DEVICE

In exploratory or gallbladder surgery, a typical surgical procedure would be to open the abdominal cavity to expose the area adjacent the liver and gallbladder. A small incision would be made in the cystic duct. Utilizing the appropriate instrument the cystic duct would be cleared of stones or slugs and the stainless steel tip 11 of the cholangiogram catheters grasped with a hemostat and the tip inserted in the cystic duct. Prior to insertion, the cholangiogram catheter would be attached to the syringe filled with the contrast medium and all of the air expelled from the syringe and the tubing of the cholangiogram catheter. This preliminary procedure is to avoid the introduction of any air into the cystic duct or the biliary tract. Air on x-rays can confuse the test by indicating or obscuring gallstones. After insertion of the stainless steel tip 11 into the cystic duct, a ligature or clamp is placed around the cystic duct and the cholangiogram catheter is withdrawn slightly bringing the flange 17 adjacent the ligature encircling the cystic duct. A tightening of the ligature securing the duct in the ligature gap 16 prevents leakage of the contrast medium or induction of air into the cystic duct. No attempt will be made to further describe any operative procedures in that they do not comprise a part of this invention. This invention pertains to the construction and arrangement of an improved cholangiogram catheter and its method of construction or assembly.

Having described in detail the components of this invention including dimensions and preferred materials, together with a device for assembling the improved cholangiogram catheter, what is desired to be claimed are all modifications of the device or methods for assembly not departing from the scope of equivalents of the device and method of assembly as defined in the appended claims.

I claim:
1. A cholangiogram catheter comprising:
   an elongated stainless steel tip having an overall length of about 0.75 inches;
   said stainless steel tip having a conical tip portion with a base diameter of about 0.091 inches and terminating in a point and a cylindrical flange at the base of said conical tip;
   a cylindrical shaft about 0.5 inches long having a diameter of about 0.035 inches projecting from the center of said cylindrical flange;
   a central passageway having a diameter of about 0.020 inches extending through said tip and said shaft and opening at the point at the first end of the conical tip portion for flowing fluid through the passageway;
   stable semi-rigid plastic tubing having an outside diameter of 0.060 to 0.065 inches and an inside diameter of 0.029 to 0.030 inches encasing and securely attached at a first end to said shaft of said tip;
   a space provided along said shaft between said flange at the base of said conical tip and the said first end of said plastic tubing;
   the spaced portion between said flange and said plastic tubing forming a ligature gap on said shaft adjacent said flange to permit tightening of a ligature around a duct or vein securing the duct or vein into the ligature gap to form a satisfactory seal against leakage or induction of air into the vein or duct; and
   a syringe adapter including a shaft attached to a second end of said plastic tubing.

* * * * *